(12) United States Patent
Netsch et al.

(10) Patent No.: US 12,131,514 B2
(45) Date of Patent: Oct. 29, 2024

(54) ANATOMICAL ENCRYPTION OF PATIENT IMAGES FOR ARTIFICIAL INTELLIGENCE

(71) Applicant: KONINKLIJKE PHILIPS N.V., Eindhoven (NL)

(72) Inventors: Thomas Netsch, Hamburg (DE); Daniel Bystrov, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 339 days.

(21) Appl. No.: 17/779,209

(22) PCT Filed: Dec. 9, 2020

(86) PCT No.: PCT/EP2020/085211
§ 371 (c)(1),
(2) Date: May 24, 2022

(87) PCT Pub. No.: WO2021/116150
PCT Pub. Date: Jun. 17, 2021

(65) Prior Publication Data
US 2022/0415004 A1 Dec. 29, 2022

Related U.S. Application Data

(60) Provisional application No. 62/946,456, filed on Dec. 11, 2019.

(51) Int. Cl.
*G06V 10/25* (2022.01)
*G06T 7/73* (2017.01)
(Continued)

(52) U.S. Cl.
CPC ................ *G06V 10/25* (2022.01); *G06T 7/74* (2017.01); *G06V 10/758* (2022.01); *G06V 10/774* (2022.01); *G06T 2207/20081* (2013.01)

(58) Field of Classification Search
CPC .... G06V 10/25; G06V 10/758; G06V 10/774; G06T 7/74; G06T 2207/20081
(Continued)

(56) References Cited

U.S. PATENT DOCUMENTS 8,384,729 B2 * 2/2013 Niwa .................. A61B 5/7435
345/581
2003/0228042 A1 12/2003 Sinha
(Continued)

FOREIGN PATENT DOCUMENTS

| EP | 3188058 A1 | 7/2017 |
|----|-----------|--------|
| EP | 3438869 A1 | 2/2019 |
| WO | 2020/173573 A1 | 9/2020 |

OTHER PUBLICATIONS

International Search Report and Written Opinion Dated Mar. 10, 2021 for International Application No. PCT/EP2020/085211 Filed Dec. 9, 2020.
(Continued)

*Primary Examiner* — Allen H Nguyen (57) ABSTRACT

An apparatus (10) for generating a training set of anonymized images (40) for training an artificial intelligence (AI) component (42) from images (11) of a plurality of persons. The apparatus includes at least one electronic processor (20) programmed to: spatially map the images of the plurality of persons to a reference image (30) to generate images (32) in a common reference frame; partition the images in the common reference frame into P spatial regions (34) to generate P sets of image patches (36) corresponding to the P spatial regions; assemble a set of training images (3) in the common reference frame by, for each training image in the common reference frame, selecting an image patch from each of the P sets of image patches and assembling the selected image patches into the training image in the common reference frame; and process the training images in the
(Continued)

common reference frame to generate the training set of anonymized images including applying statistical inverse spatial mappings to the training images in the common reference frame, wherein the statistical inverse spatial mappings are derived from spatial mappings (33) of the images of the plurality of persons to the reference image.

20 Claims, 6 Drawing Sheets

(51) Int. Cl.
  *G06V 10/75* (2022.01)
  *G06V 10/774* (2022.01)
(58) Field of Classification Search
  USPC .......................................................... 382/173
  See application file for complete search history.

(56) References Cited

U.S. PATENT DOCUMENTS

| | | | |
|---|---|---|---|
| 2007/0127790 A1* | 6/2007 | Lau | G06F 16/58 |
| | | | 382/128 |
| 2010/0061606 A1* | 3/2010 | Geiger | G16H 30/20 |
| | | | 382/128 |
| 2012/0166211 A1* | 6/2012 | Park | G16H 50/20 |
| | | | 705/2 |
| 2018/0271460 A1 | 9/2018 | Geiger | |
| 2019/0043611 A1 | 2/2019 | Saalbach | |
| 2020/0167930 A1* | 5/2020 | Wang | G06N 3/08 |
| 2021/0049756 A1* | 2/2021 | He | G06N 3/04 |

OTHER PUBLICATIONS

Pranav Dar: "25 Open Datasets for Deep Learning Every Data Scientist Must Work With", Mar. 29, 2018 https://www.analyticsvidhya.com/blog/2018/03/comprehensive-collection-deep-learning-datasets/.

Franz, et al: "Precise anatomy localization in CT data by an improved probabilistic tissue type atlas", Proceedings vol. 9784, Medical Imaging 2016: Image Processing; 978444 (2016).

GAN 2.0: NVIDIA's Hyperrealistic Face Generator, 2018 https://medium.com/syncedreview/gan-2-0-nvidias-hyperrealistic-face-generator-e3439d33ebaf.

Karras: "A Style-Based Generator Architecture for Generative Adversarial Networks", 2019 https://arxiv.org/pdf/1812.04948.pdf.

* cited by examiner

ANATOMICAL ENCRYPTION OF PATIENT IMAGES FOR ARTIFICIAL INTELLIGENCE

CROSS REFERENCE TO RELATED APPLICATIONS

This application is the U.S. National Phase application under 35 U.S.C. § 371 of International Application No. PCT/EP2020/085211 filed Dec. 9, 2020, which claims the benefit of U.S. Provisional Patent Application No. 62/946,456 filed Dec. 11, 2019. These applications are hereby incorporated by reference herein.

FIELD

The following relates generally to the image processing arts, medical image diagnostic analysis arts, patient anonymization arts, artificial intelligence (AI) arts, and related arts.

BACKGROUND

AI is becoming increasingly used in the analysis of medical images. For example, an AI classifier can be used to detect lesions, to classify an image as to whether it depicts a certain medical condition, and so forth. An AI component is usually trained using a set of training images, which are often labeled by a clinical expert as to the "correct" classification (supervised training). For example, clinical images with and without tumors may be used as the training set, with a clinician labeling the tumors. The AI component is then trained to maximize the accuracy with which it discriminates between images with versus without tumors.

A problem arises, however, in that the training images may be considered personally identifiable patient data. Even if the metadata associated with the images are anonymized, the images themselves can potentially be identified to specific individuals, and moreover may contain information about a medical condition of the individual. The trained AI component can potentially embed the training images. Hence, an AI component trained on clinical patient images may be prohibited from distribution by applicable patient privacy regulations. This could be overcome by obtaining patient consent to use the images in the training, but it can be difficult to build up a sufficiently large and diverse training set in this way, and to maintain an auditable record of all the associated patient consent documents. Another approach is to synthesize training images, for example using a model of the anatomy and a model of the imaging physics producing the synthesized training image, but synthesized images may differ from real clinical images in ways that may not be apparent to human reviewers but that may introduce systematic error into the resulting trained AI component.

The following discloses certain improvements to overcome these problems and others.

SUMMARY

In one aspect, an apparatus for generating a training set of anonymized images for training an AI component from images of a plurality of persons. The apparatus includes at least one electronic processor programmed to: spatially map the images of the plurality of persons to a reference image to generate images in a common reference frame; partition the images in the common reference frame into P spatial regions to generate P sets of image patches corresponding to the P spatial regions; assemble a set of training images in the common reference frame by, for each training image in the common reference frame, selecting an image patch from each of the P sets of image patches and assembling the selected image patches into the training image in the common reference frame; and process the training images in the common reference frame to generate the training set of anonymized images including applying statistical inverse spatial mappings to the training images in the common reference frame, wherein the statistical inverse spatial mappings are derived from spatial mappings of the images of the plurality of persons to the reference image.

In another aspect, a non-transitory computer readable medium stores instructions executable by at least one electronic processor for performing a method of generating a training set of anonymized images for training an AI component from images of a plurality of persons. The method includes: partitioning the images into P spatial regions to generate P sets of image patches corresponding to the P spatial regions; assembling a set of training images in a common reference frame by, for each training image in the common reference frame, selecting an image patch from each of the P sets of image patches and assembling the selected image patches into the training image; and processing the training images in the common reference frame to generate the training set of anonymized images.

In another aspect, a method of generating a training set of anonymized images for training an AI component from images of a plurality of persons. The method includes: partitioning the images into P spatial regions to generate P sets of image patches corresponding to the P spatial regions; assembling a set of training images in a common reference frame by, for each training image in the common reference frame, selecting an image patch from each of the P sets of image patches and assembling the selected image patches into the training image; processing the training images in the common reference frame to generate the training set of anonymized images; and training the AI component of the medical diagnostic device on the training set of anonymized images.

One advantage resides in generating a training image dataset from patient images using only portions of several patient images.

Another advantage resides in generating a training image dataset from patient images without patient specific information being able to be extracted from the images.

Another advantage resides in anonymizing image content of patient images in a non-reversible manner.

Another advantage resides in anonymizing image content of patient images before using the images to train an AI component.

Another advantage resides in generating a training image dataset in which each training image comprises portions of multiple patient images from different patients.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

The following proposes systems and methods to anonymize real clinical images (and not just the associated metadata). To do this, the following process is disclosed. First, a set of real clinical images $\{R\}_{r=1,\ldots,R}$ are spatially mapped to a reference image. The reference image may be a clinical atlas image, or it may be a "typical" clinical image (optionally taken from the set $\{R\}$). The spatial mapping, for example, will typically be a non-rigid spatial registration, and will result in a spatial transform $Z_r$ for each image $r \in \{R\}$. The result is a set of spatial transforms $\{Z_r\}_{r=1,\ldots,R}$ (or $\{Z_r\}_{r=1,\ldots,R-1}$ if one image is taken as the reference image).

Next, the spatially mapped images are partitioned into a set of spatial regions $\{P\}_{p=1,\ldots,P}$. The set of spatial regions $\{P\}$ may be defined using a rectilinear grid, or the spatial regions may be defined along anatomical lines. This provides R patches corresponding to each spatial region p of the set of spatial regions $\{P\}$.

Then, a set of training images $\{N\}_{n=1,\ldots,N}$ is constructed. Each training image $n \in \{N\}$ is constructed by randomly selecting one of the R patches corresponding to each spatial region p, and then assembling the selected patches into the training image n. The resulting N patch-formed images are in the reference image space, which is undesirable as it does not capture the realistic distribution of sizes and shapes of the imaged anatomy. To address this, a randomly selected inverse transform is applied to each patch-formed image. In one approach, the randomly selected inverse transform is randomly selected from the set of spatial transforms $\{Z_r\}$. In another approach, statistical distributions of the parameters of the spatial transforms of the set $\{Z_r\}$ is determined, and the inverse transforms are generated using these distributions.

A problem that can arise in this approach is that the boundaries of the patches can be discontinuous in the training images. For example, a limb bone may exhibit an artificial "break" at the boundary between two adjacent spatial regions. Whether this is a problem can depend on the nature of the AI component being trained. (Obviously, if the AI is being trained to detect broken limb bones, this would be a problem; whereas, if the AI is being trained to detect small lesions then the likelihood of this patch boundaries being mistaken by the AI for a lesion may be low).

Two approaches are disclosed for addressing this issue. A first embodiment includes a process to perform smoothing at the boundaries. This might be most easily done prior to applying the inverse transform, as the boundary locations are the same for each patched image prior to the inverse transform. In a second embodiment, the set of spatial regions $\{P\}$ is designed to avoid having spatial region boundaries cut across major anatomical boundaries. For example, the liver of the reference image may be divided into a subset of spatial regions that are all entirely within the liver; each lung may be divided into a subset of spatial regions that are all entirely within that lung; and so forth. This embodiment allows for avoiding spatial region boundaries crossing anatomical boundaries, and is feasible since the set of spatial regions $\{P\}$ is only delineated once, and the same set of spatial regions $\{P\}$ is then applied to each of the $\{P\}$ clinical images to generate the patches.

In some embodiments disclosed herein, the performance of the AI component trained on the patched training set $\{N\}$ can be readily graded by comparing its performance with an analogous AI component that is trained on the original set of clinical images $\{R\}$. The latter analogous AI component (which could potentially contain personally-identifying image information) would be discarded after its use as a benchmark, and the AI component trained on the patched training set $\{N\}$ would be distributed to customers.

The disclosed systems and methods may not be limited to training an AI component to analyze medical images, but could more generally be applied to the training of any AI image analysis component that will be trained on a set of training images that all have the same basic layout (e.g., face images used for training a facial recognition AI, or images of persons used to train an AI to classify an attribute of a photographed person, or retinal scan images used in training a retinal scanner to perform user identification, are further examples of situations where the disclosed approach may be useful). Moreover, the approach is applicable to either two-dimensional or three-dimensional (i.e. volumetric) images. In the case of volumetric images, the set of spatial regions $\{P\}$ will be defined over a volume, and the image patches will be volumetric image patches.

Figure 1:
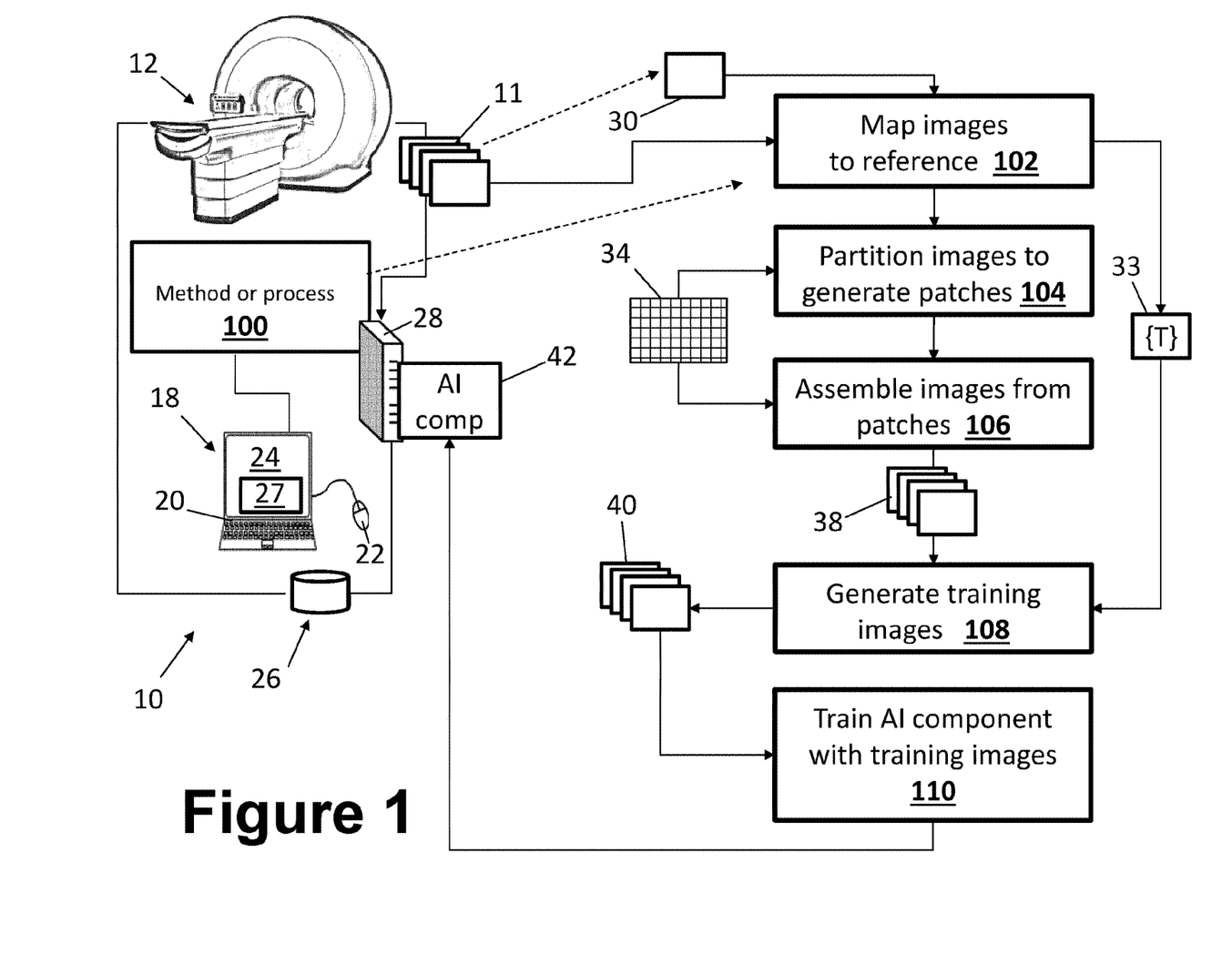
FIG. 1 diagrammatically illustrates an illustrative apparatus generating a training set of anonymized images for training an AI component from images of a plurality of persons in accordance with the present disclosure.

With reference to FIG. 1, an illustrative apparatus 10 for generating a training set of anonymized training images 40 for training an AI component 42 from images 11 of a plurality of persons is shown. For example, the apparatus 10 can receive images 11 of a plurality of persons from an image acquisition device (also referred to as an imaging device) 12. The imaging device 12 can acquire the images 11 as medical images of an anatomy. In this example, the image acquisition device 12 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. Additionally, or alternatively, the imaging device 12 can be a camera (e.g., video, RBG, infrared, and so forth), in which case the images 11 are portrait images, or a retinal scanner, in which case the images are retinal images, or so forth, as appropriate for the particular AI component 42 to be trained. It is to be understood that the illustrative imaging device 12 is representative, and that more generally the set of images 11 may be acquired by a number of different imaging devices. For example, the images 11 may be collected from a database such as a Picture Archiving and Communication System (PACS) or other medical images repository 28 that may service a hospital, a network of hospitals, or other entity. The images of the set of images 11 all have the same basic layout. For example, in the case of clinical images, the images 11 are all of the same imaging modality and the same anatomical part (e.g. all head MRI images, all liver MRI images, all chest CT images, or so forth) and all of the same or similar orientation (e.g., all sagittal head MRI images, or all coronal head MRI images, or so forth) and using the same or similar imaging conditions (e.g. all using the same contrast agent, or all using no contrast agent) or imaging conditions that span the operational space of imaging conditions for which the AI component is to be used. As another example, for use in training a retinal scanner the images 11 may be all retinal images. As another example, for use in training a facial recognition system, the images 11 may be all portrait face images. Furthermore, the images 11 should be statistically representative of the demographic range and medical condition or conditions that are to be handled by the AI component 42 that is to be trained. If there are known confounding medical conditions that might cause a misdiagnosis (or other erroneous output) by the AI, then the set of images 11 may include examples of such confounding conditions. For example, if the images 11 are mammogram images and it is expected that a skin fold in a mammogram image might adversely impact operation of the AI component 42, then the set of (here, mammogram) images 11 may optionally include some mammogram images with skin folds so as to improve robustness of the resulting trained AI component.

FIG. 1 also shows an electronic processing device 18, such as a workstation computer, or more generally a computer. Alternatively, the electronic processing device 18 can be embodied as a server computer or a plurality of server computers, e.g. interconnected to form a server cluster, cloud computing resource, or so forth. The workstation 18 includes typical components, such as an electronic processor 20 (e.g., a microprocessor), at least one user input device (e.g., a mouse, a keyboard, a trackball, and/or the like) 22, and a display device 24 (e.g. an LCD display, plasma display, cathode ray tube display, and/or so forth). In some embodiments, the display device 24 can be a separate component from the workstation 18.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 27 for display on the display device 24.

The apparatus 10 also includes, or is otherwise in operable communication with, the database 28 storing the images 11. The database 28 can be any suitable database, including a Radiology Information System (RIS) database, a Picture Archiving and Communication System (PACS) database, an Electronic Medical Records (EMR) database, and so forth. The database 28 can, for example, be implemented by a server computer and the non-transitory medium or media 26. The workstation 18 can be used to access the stored images 11. It will also be appreciated that the images 11 can, as previously noted, be acquired by a number of imaging devices, and not necessarily by only the representative one illustrated image acquisition device 12.

The apparatus 10 is configured as described above to perform a method or process 100 for generating a training set of anonymized images. The non-transitory storage medium 26 stores instructions which are readable and executable by the at least one electronic processor 20 to perform disclosed operations including performing the method or process 100 for generating a training set of anonymized images. In some examples, the method 100 may be performed at least in part by cloud processing.

As shown in FIG. 1, and with references to FIGS. 2-7, an illustrative embodiment of imaging examination workflow visualization method 100 is diagrammatically shown as a flowchart. FIGS. 2-7 show examples of outputs of the operations of the method 100. The images shown in FIGS. 2-7 are two-dimensional X-ray images of a chest, but it will be appreciated that the method 100 can apply for any suitable imaging modality or anatomical region of a patient. Without loss of generality, it is assumed that the images 11 form a set {R}, that is, there are R images in the set of images 11. Although not shown in FIG. 1, it is assumed that the metadata associated with the images 11 is stripped, or at least any personally identifying information (PII) contained in the metadata associated with the images 11 is stripped. Again, without loss of generality, the generated set of anonymized training images 40 is assumed to form a set {N}, that is, there are N anonymized training images. In general, there is no relationship between R and N, except that the number R of images 11 should be large enough compared with the number N of anonymized training images 40 so that the patches formed by partitioning the R images 11 into the spatial regions P are "well mixed" in the anonymized training images 40. (To illustrate this, if for example there are only R=5 images 11, and N=100 training images 40 are to be generated, then at least some training images will likely consist of patches mostly drawn from a single one of the five input images 11, which is undesirable. On the other hand, if R=1000 and N=20 then it is likely that no anonymized training image will contain more than one or two patches taken from any single one of the 1000 source images 11).

At an operation 102, the at least one electronic processor 20 is programmed to spatially map the images 11 of the plurality of persons to a reference image 30 to generate images 32 in a common reference frame. When the images 11 are medical images, the reference image 30 can be an anatomical atlas image of the anatomy. When the images 11 are portrait images, the reference image 30 can be a facial atlas image. Alternatively, in either of these examples, the reference image 30 can be one of the images 11 of the plurality of persons (this option is diagrammatically indicated in FIG. 1). The reference image 30 in this latter case may be selected from the set of images 11 manually—for example, a "typical" image is preferably chosen as the reference image. (Typical, in this case, suitably being an image of anatomy of average size, and preferably without any significant abnormalities).

Figure 2:
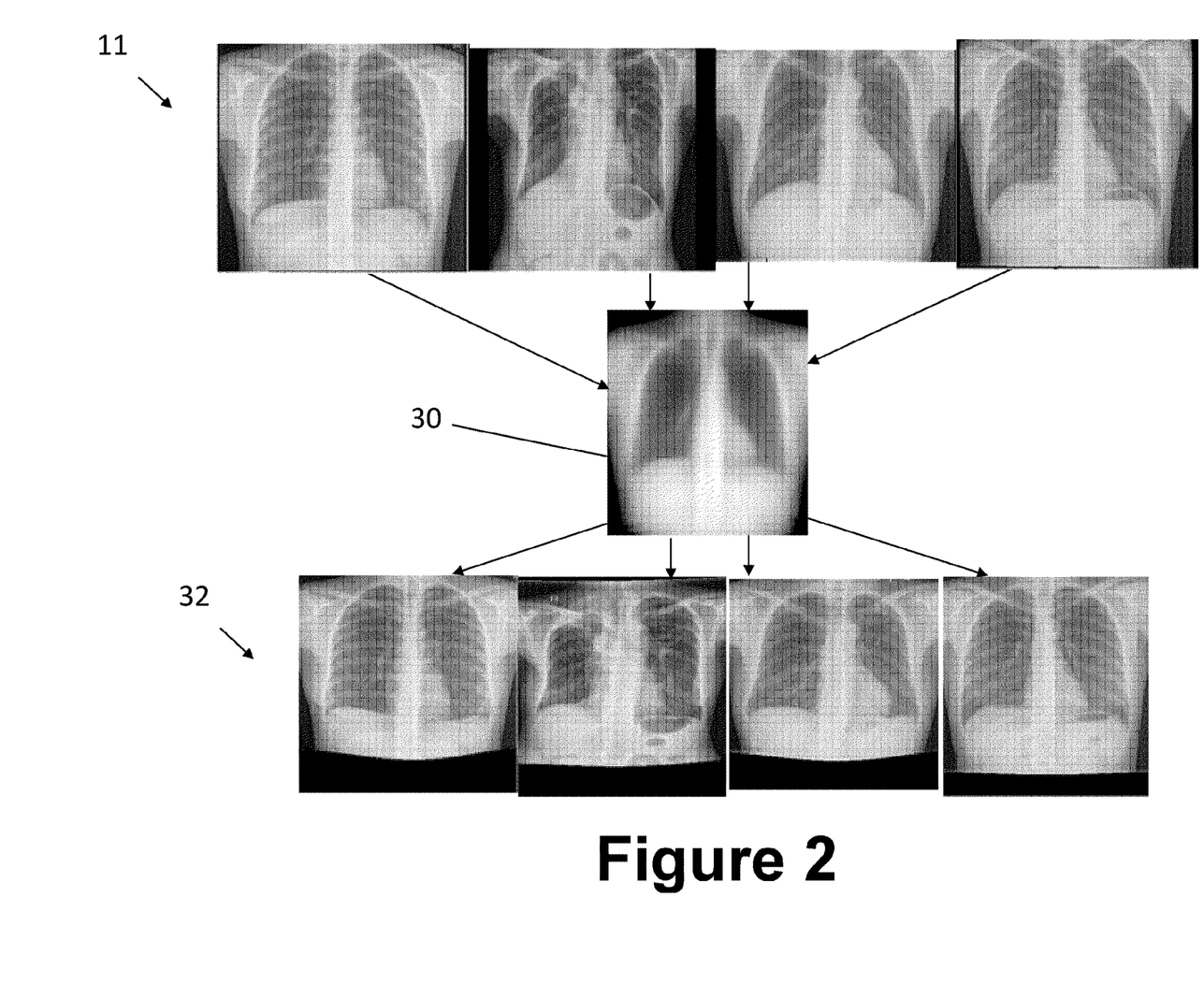
FIGS. 2-7 show examples of images generated by the apparatus of FIG. 1.

FIG. 2 shows an example of the operation 102. Four images 11 are acquired by the imaging device 12 and/or retrieved from the database 28. Each of the four images 11 shown are from different patients (shown at the "top" of FIG. 2). The images 11 are mapped to a reference image 30 (which in this case is an atlas image, and is shown in the "middle" of FIG. 2). The mapping can be performed with any suitable mapping algorithm known in the art (such as the one described in A. Franz, et al., Precise anatomy localization in CT data by an improved probabilistic tissue type atlas. SPIE Medical Imaging: Image Processing, volume 9784, 978444, 2016). This Franz method provides a non-linear mapping function which allows mapping all images 11 to a common atlas reference 30. After the mapping, all images 32 in a common reference frame are comparable, e.g., a location/pixel in one image relates to a corresponding anatomical location in all other images. These images 32 are shown at the "bottom" of FIG. 2.

The mapping operation 102 also outputs a set of mappings or transforms 33. In one approach, the mapping of each image of the set of images 11 to the reference image 30 is one mapping of the set of mappings 33. This results in R mappings 33 (or, possibly, R-1 mappings if the reference image 30 is one of the R images 11). In another approach, the set of mappings 33 is output as a multi-dimensional statistical distribution. For example, if the mapping operation 102 employs a parameterized mapping algorithm, then the distribution of each parameter in the R mappings of the respective R images 11 to the reference image 30 is represented by (for example) the mean and standard deviation of a Gaussian fit to the distribution of the parameter.

At an operation 104, the at least one electronic processor 20 is programmed to partition the images 32 in the common reference frame into a number (designated, without loss of generality, as P) of spatial regions 34 to generate P sets of image patches 36 corresponding to the P spatial regions. In some embodiments, the P spatial regions 34 form a rectilinear grid, while in other embodiments, the P spatial regions 34 align with regions of interest in the reference image 30, such as anatomical boundaries between organs in the reference image 30. In this embodiment, when the images 11 are medical images, boundaries of the P spatial regions 34 do not cross anatomical boundaries of the anatomy in the reference image 30. The set {P} of spatial regions 34 are pre-defined, either automatically (e.g. using a computer-generated rectilinear grid) or manually drawn, for example, drawn on the reference image 30 using a contouring GUI 27 such as that used in contouring organs for radiation therapy planning. A hybrid approach is also contemplated, in which boundaries of major organs are manually drawn using the contouring GUI 27 to define coarse spatial regions aligning with organs or other anatomical structures, and then each coarse spatial region is itself automatically partitioned into a computer-generated rectilinear grid thereby defining the final set of P spatial regions 34.

The set of spatial regions 34 is suitably chosen to ensure anonymity of the resulting anonymized training images 40. To this end, the spatial regions 34 should be chosen to be small enough so that no single patch 36 is personally identifying. Furthermore, the number of spatial regions (P) should be large enough so that there is a statistically negligible chance that most or all the randomly selected patches that making up a given training image will come from a single image of the set of images 11. Furthermore, it is useful for the number R of images 11 to be larger (and preferably much larger) than the number of spatial regions P, which again reduces the likelihood that most or all the randomly selected patches that making up a given training image will come from a single image of the set of images 11.

Figure 3A:
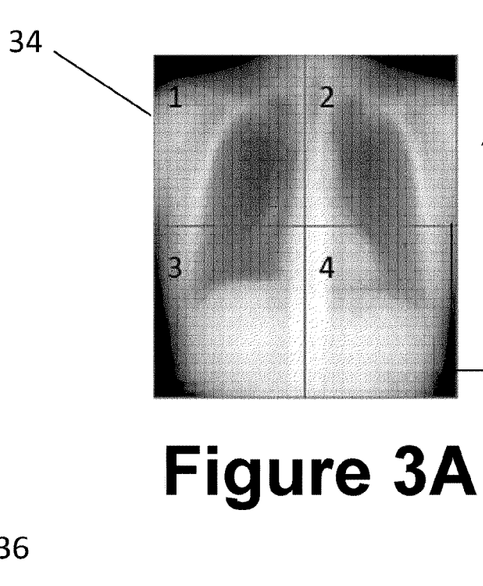
Figure 3B:
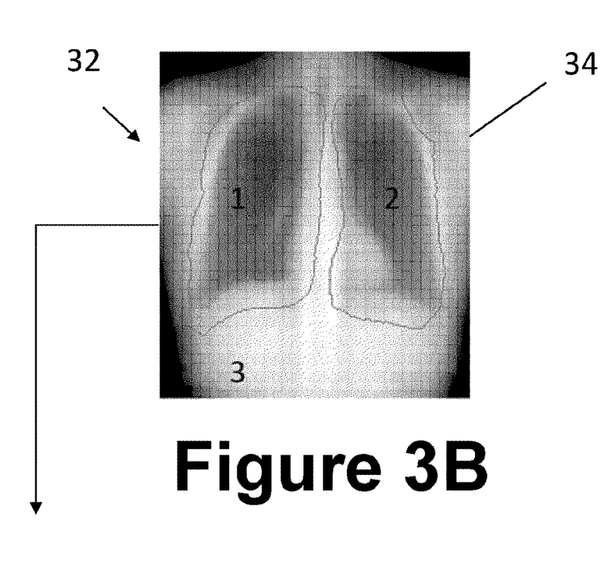
Figure 4:
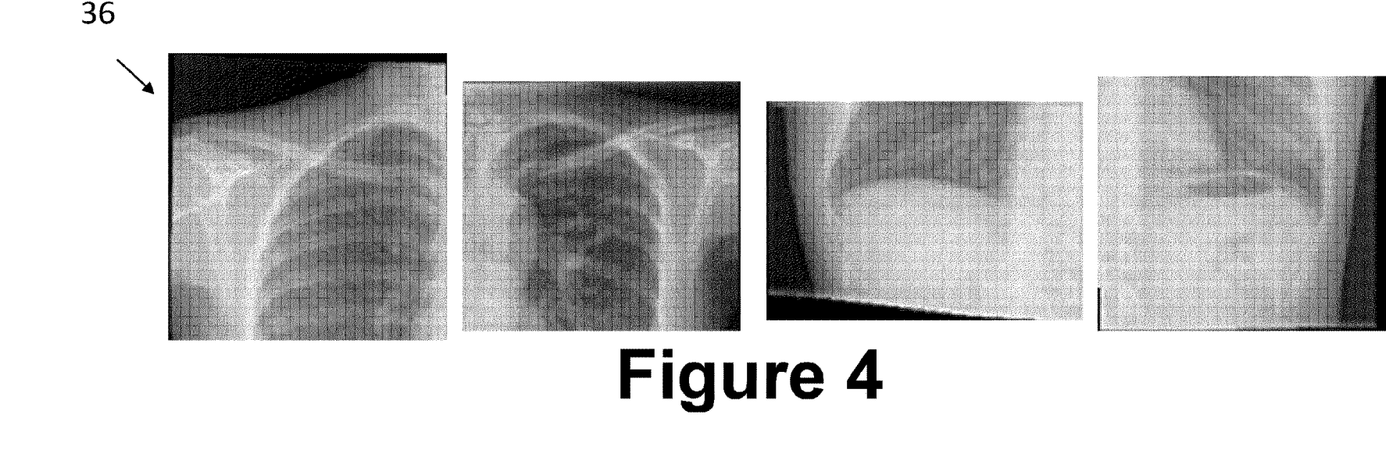

FIGS. 3A, 3B, and 4 show two examples of the operation 104. As shown in FIGS. 3A and 3B, the images 32 in the common reference frame are divided into multiple spatial regions 34. FIG. 3A shows an example of the embodiment where the spatial regions 34 form a rectilinear grid (e.g., 4 spatial regions are illustrated, and are of identical size), while FIG. 3B shows an example of the embodiment in which the spatial regions 34 align with regions of interest in the reference image 30 (e.g., only 3 spatial regions are illustrated). It should be noted that as used herein, the "spatial regions" designate the spatial delineations used in dividing the images 11 into patches. The term "patch" as used herein then refers to the portion of a given divided image 11 corresponding to a given spatial region. Since there are R images 11, the partitioning operation 104 will produce R patches corresponding to each spatial region of the set of P spatial regions 34. There will be P sets of patches corresponding to the P spatial regions, with each set of patches consisting of R patches. The spatial regions 34 are applied to the images 32 in the common reference frame to generate the patches 36, as shown in FIG. 4. Each patch 36 can be identified as a tuple including (image identifier, patch number). The image identifier is preferably not personally identifying. Rather, for example, the R images can simply be numbered 1, . . . ,R and the number assigned to the image is then is the image identifier. Each patch 36 corresponding to a given spatial region 34 is anatomically comparable between the images 32 in the common reference frame.

Figure 5:
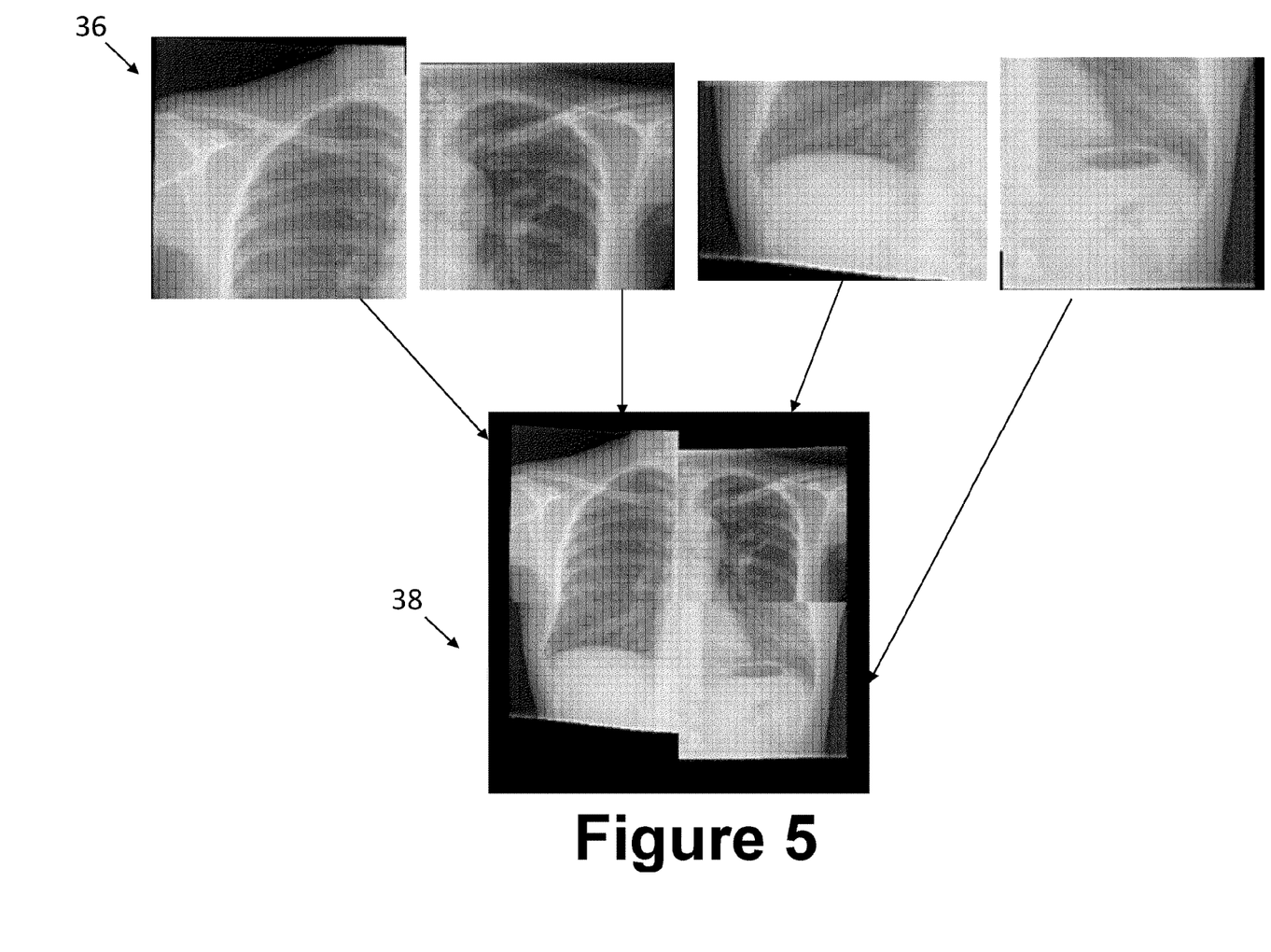

At an operation 106, the at least one electronic processor 20 is programmed to assemble a set of training images 38 in the common reference frame (see also FIG. 5). To do so, an image patch 36 is selected from each of the P sets of image patches for each training image 38 in the common reference frame. The selected image patches 36 are assembled into the training image 30 in the common reference frame, in accordance with the spatial layout of the set of spatial regions 34. In some examples, the selecting of the image patch 36 from each of the P sets of image patches includes randomly or pseudorandomly selecting an image patch. As used herein, the term "pseudorandom" and similar nomenclature has its usual and ordinary meaning in the computer science arts, and refers to a process that is technically deterministic but which produces results that are statistically similar to a random process and that are not repeated for multiple runs of the pseudorandom process. For example, a common pseudorandom value generator comprises a numbers sequence generator that produces a deterministic sequence of numbers having statistics similar to a true random sequence of numbers, and which is long (possibly infinitely long). For each run, a seed is chosen which determines the starting point in the sequence. The seed may be chosen, for example, based on a set of low bits the computer clock value at the instant the run begins, which is essentially a random number for a high-speed computer processor running at gigahertz speed or higher. Other pseudorandom generators, such as Monte Carlo simulation methods, are also suitable. Furthermore, the term "random" as used herein is to be understood as encompassing implementations employing pseudorandom value generators.

FIG. 5 shows an example of the operation 106. For each spatial region 34, a random image identifier is selected by, for example, a random number generator, and the patch of the set of R patches 36 corresponding to that spatial region with that image identifier is selected. This is repeated for each spatial region of the set of P spatial regions 34. The selected patches 36 are thus generally from different images of the set of images 11, and are assembled using the spatial regions 34 (see FIG. 3) to generate the set of training images 38 in the common reference frame. The training image 38 in the common reference frame shown in FIG. 4 includes patches 36 from 4 different patients. In practice, the number of patches P is likely to be much larger than 4.

In the above approach, there is some possibility that two (or even more) patches from a single image of set of the images 11 may be included in a single one of the training images 38 in the common reference frame. This is unlikely to be a problem so long as the number R of images 11 is much larger than the number P of spatial regions, and preferably also much larger than the number N of resulting training images 40. However, if it is desired to ensure that no single one of the training images 38 in the common reference frame has more than one patch from a single image 11 then the final set of patches assembled for each training image can be checked for duplicates (i.e. two or more patches from a single image 11). If such a duplicate is found, the training image in the common reference frame is discarded. This approach requires that R>P holds, and preferably should have R>>P.

The operation 106 is repeated until a desired number N of training images 38 in the common reference frame are assembled. The training images 38 in the common reference frame are anonymized. However, they are not representative of the statistical variation of size/shape of persons (or their imaged anatomical portions) in the set of images 11. This is a consequence of the mapping operation 102, which leads to the training images 38 all being in the common reference frame of the reference image 30.

Accordingly, at an operation 108, the at least one electronic processor 20 is programmed to process the training images 38 in the common reference frame to generate a training set of anonymized images 40, which is representative of the statistical variation of size/shape of persons (or their imaged anatomical portions) in the set of images 11. To do so, statistical inverse spatial mappings are applied to the training images 38 in the common reference frame. The statistical inverse spatial mappings are derived from the spatial mappings 33 of the images 11 of the plurality of persons to the reference image 30. In one example, spatial mappings 33 of the images 11 to the reference image 30 are inverted to form a set of inverse spatial mappings, from which the statistical inverse spatial mappings are selected randomly or pseudo-randomly. In another example, statistical distributions of parameters of the spatial mappings 33 of the images 11 are computed to form the set of inverse spatial mappings, and the statistical inverse spatial mappings are generated from these statistical distributions. Optionally, the operation 108 can further include a smoothing operation that can be performed at boundaries of the image patches 36 to further generate the training set of anonymized images 40.

Figure 6:
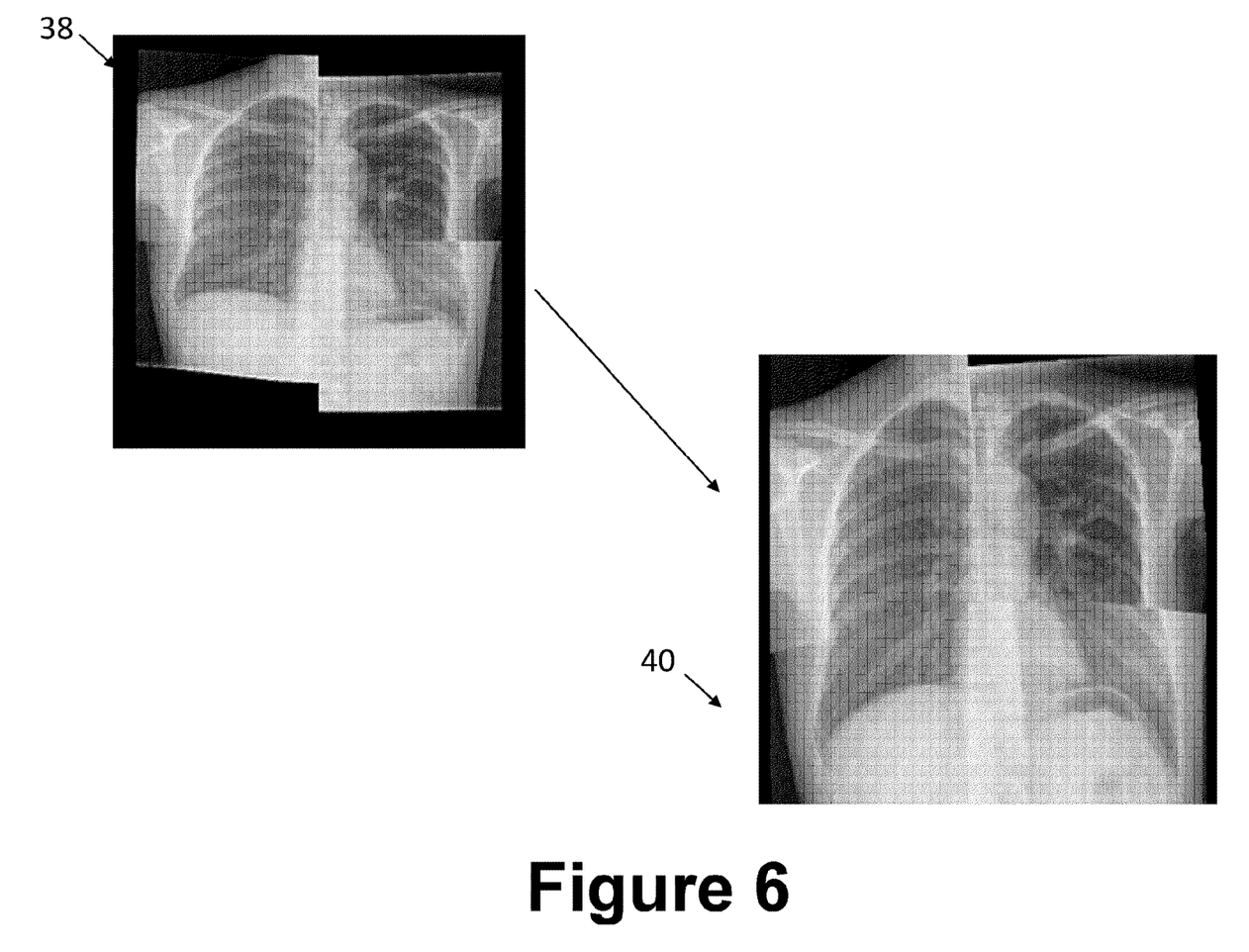

FIG. 6 shows an example of the operation 108. The training image 38 in the common reference frame is re-mapped to the original patient image space of the images 11 (see FIG. 2) by applying the inverse atlas mapping. One of the mappings calculated in at the operation 102 is randomly selected, inverted, and applied to the training image 38 in the common reference image 30 space to generate the training set of anonymized images 40.

FIG. 6 also shows an example of one of the anonymized images 40. However, the anonymized image 40 may not have edges of the patches 36 that anatomically perfectly fit with each other. As shown in FIG. 6, the patches 36 in the upper right corner and the lower right corner introduce an offset visible at the border of the lung. This offset can be explained by variation of image intensities in the original images 11 and/or an imperfect mapping algorithm. The resulting anonymized images 40 should be as close as possible to real patient scan. Therefore, both image intensities and edge structures at the border of the patches 36 are optionally repaired by using smoothing or other suitable image processing techniques. Intensity values, for example can be corrected by adapting the intensity means calculated in the vicinity of the patch borders, unmatched edges can be locally shifted by a non-linear image transform. The operations 106 and 108 can be repeated to generate a new database of anonymized images 40. The original images 11 can then no longer be reconstructed from the set of anonymized images 40.

The operations 104-108 are described above as being performed in the context of anatomical image correlation. However, these operations 104-108 can be performed in the context of functional image correlation. That is, patches 36 from images with matching patterns of functional data can be combined to form the training images 38. To do so, a pattern recognition operation is performed to the set of images 11 to form a subgrouping of images with correlated functional data across the patches 36. This subgrouping of patches 36 are used to form the training images 38. The pattern recognition operation and subgrouping formation, which is done prior to the creation of the training images 38 (i.e., operation 108) can be used in in anatomical images, to improve the correlation of the patches, such as by patient/organ size, disease state, location of abnormality or clinical impact, etc. This data can come from the image analysis, or supplemented with patient data, e.g. from patient clinical records.

In some examples, the PACS database 28 can receive images 11 from multiple imaging devices 12, which can be located at one or more medical institutions. Patches 36 from these images can be stored with a subgroup specification until sufficient image data for meeting a subset criteria is available to create additional training images 38.

Referring back to FIG. 1, at an operation 110, the at least one electronic processor 20 is programmed to train the AI component 42 on the training set of anonymized images 40. The trained AI component 42 can be deployed in the workstation 18 for use as part of a computer-aided clinical diagnostic workstation (e.g. a radiology workstation used by radiologists in interpreting imaging examinations). The anatomy images 11 can be used to train the AI component 42 of a medical diagnostic device, while the portrait images 11 can be used to train the AI component 42 of a facial recognition device (for example, with the AI being deployed in a facial recognition scanner used to control access to a restricted area). As yet another example, if the images 11 are retinal images, then the trained AI component 42 may be deployed in a retinal scanner used to control access to a restricted area. These are merely some illustrative applications.

In some examples, the operation 110 can include validating the training of the AI component 42 on the training set of anonymized images 40. To do so, the AI component 42 is trained on the training set of images 40 to generate a trained AI component. A separate instance of the AI component 42 is trained on the original images 11 to generate a reference trained AI component. The performance of the AI component 42 trained on the training set of anonymized images 40 is validated by comparing performance of the trained AI component trained on the training set of anonymized images 40 with performance of the reference trained AI component (i.e., trained on the original images 11).

Figure 7:
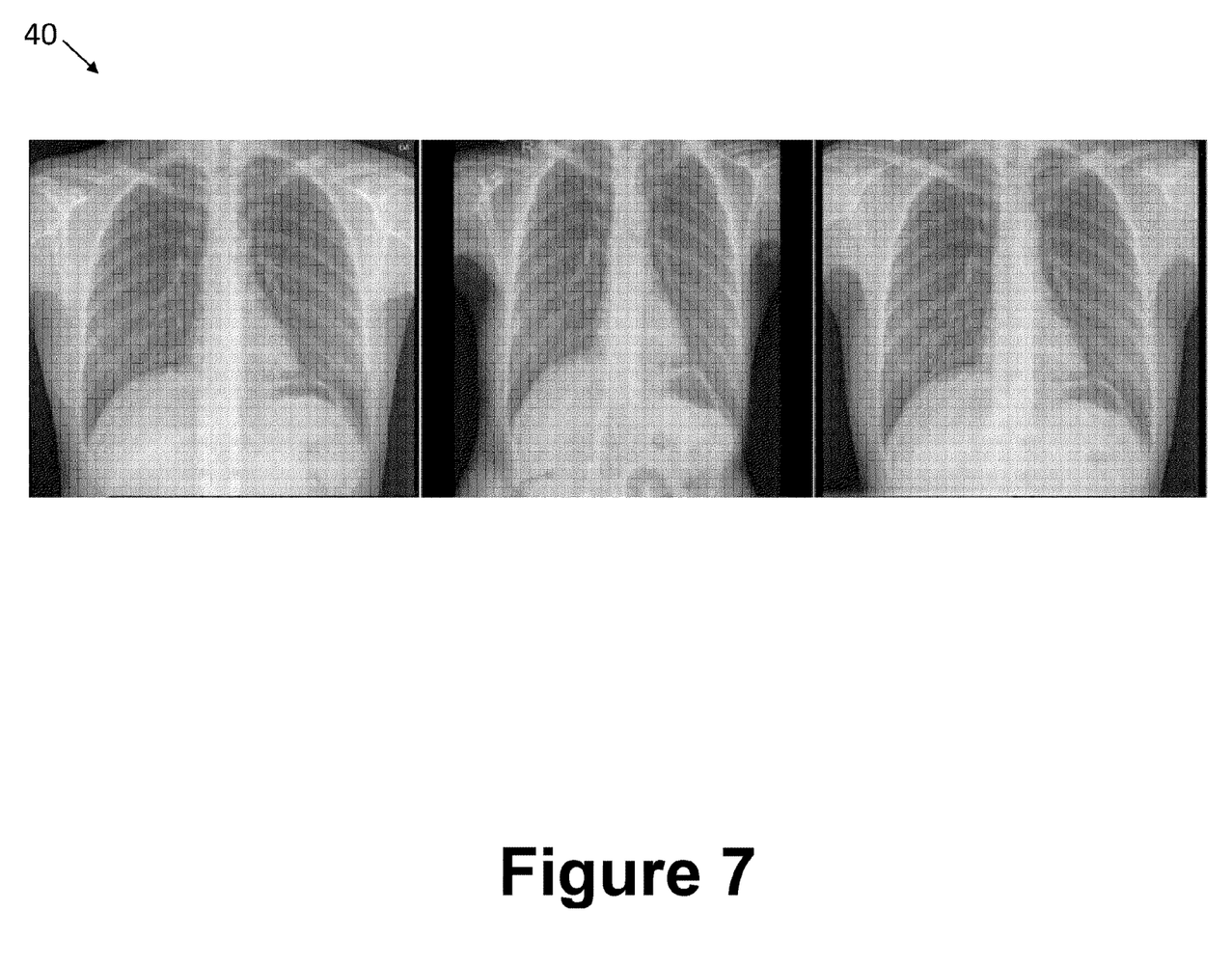

In general, the number of spatial regions P can be increased to provide a higher degree of anonymization of the anonymized images 40. As previously noted, the set of spatial regions 34 can have various spatial geometries and layouts. For example, "puzzle-like" shapes, patterns, decomposition tiling can be used to define the spatial regions 34. In particular, the spatial regions can be defined in the reference image 30 in such a way so that the borders of the spatial regions 34 do not cut through anatomical edges, or at least cut through anatomical edges orthogonally. FIG. 7 shows an example of anonymized images generated using such tiling. This may still result in errors at boundaries between spatial regions 34, but they are greatly reduced and can be more easily corrected by smoothing or other image processing.

In some embodiments, to further anonymize the original images 11, as previously mentioned a mean and variance of all mappings 33 can be calculated. From these, a random inverse mapping can be generated which further increases a degree of anonymization.

In other embodiments, when the patches 36 are merged, the image content or anatomical type (e.g., gender) can be taken into account, so that only similar patient patches are merged together. In another example, registration algorithms can be sued to merge the patches 36.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for generating a training set of anonymized images for training an artificial intelligence (AI) component from images of a plurality of persons, the apparatus including at least one electronic processor programmed to:
spatially map the images of the plurality of persons to a reference image to generate images in a common reference frame;
partition the images in the common reference frame into P spatial regions to generate P sets of image patches corresponding to the P spatial regions;
assemble a set of training images in the common reference frame by, for each training image in the common reference frame, selecting an image patch from each of the P sets of image patches and assembling the selected image patches into the training image in the common reference frame; and
process the training images in the common reference frame to generate the training set of anonymized images including applying statistical inverse spatial mappings to the training images in the common reference frame, wherein the statistical inverse spatial mappings are derived from spatial mappings of the images of the plurality of persons to the reference image.

2. The apparatus of claim 1, wherein the images of the plurality of persons are medical images of an anatomy, and the reference image is an anatomical atlas image of the anatomy.

3. The apparatus of claim 1, wherein the images of the plurality of persons are portrait images, and the reference image is a facial atlas image.

4. The apparatus of claim 1, wherein the reference image is one of the images of the plurality of persons.

5. The apparatus of claim 1, wherein the P spatial regions form a rectilinear grid.

6. The apparatus of claim 1, wherein the P spatial regions align with regions of interest in the reference image.

7. The apparatus of claim 5, wherein the images of the plurality of persons are medical images of an anatomy, and boundaries of the P spatial regions do not cross anatomical boundaries of the anatomy in the reference image.

8. The apparatus of claim 1, wherein the selecting of an image patch from each of the P sets of image patches comprises randomly or pseudorandomly selecting an image patch from each of the P sets of image patches.

9. The apparatus of claim 8, wherein the selecting of an image patch from each of the P sets of image patches comprises randomly or pseudorandomly selecting an image patch from each of the P sets of image patches with matching functional data patterns.

10. The apparatus of claim 1, wherein:
the at least one electronic processor is further programmed to invert the spatial mappings of the images of the plurality of persons to the reference image to form to a set of inverse spatial mappings, and
the statistical inverse spatial mappings are randomly or pseudorandomly selected from the set of inverse spatial mappings.

11. The apparatus of claim 1, wherein:
the at least one electronic processor is further programmed to compute statistical distributions of parameters of the spatial mappings of the images of the plurality of persons to the reference image to form to a set of inverse spatial mappings; and
the statistical inverse spatial mappings are generated based on the statistical distributions of parameters of the spatial mappings of the images of the plurality of persons to the reference image.

12. An apparatus for training a medical diagnostic device, the apparatus comprising
the at least one electronic processor programmed to generate a training set of anonymized images from images of a plurality of persons as set forth in claim 1, wherein the images of the plurality of persons are medical images of an anatomy;
wherein the at least one electronic processor is further programmed to train an artificial intelligence (AI) component of the medical diagnostic device on the training set of anonymized images.

13. An apparatus for training a facial recognition device, the apparatus comprising
the at least one electronic processor programmed to generate a training set of anonymized images from images of a plurality of persons as set forth in claim 1, wherein the images of the plurality of persons are portrait images;
wherein the at least one electronic processor is further programmed to train an artificial intelligence (AI) component of the facial recognition device on the training set of anonymized images.

14. An apparatus for training and validating a trained artificial intelligence (AI) component, the apparatus comprising
the at least one electronic processor programmed to generate a training set of anonymized images from images of a plurality of persons as set forth in claim 1;
wherein the at least one electronic processor is further programmed to:
train the AI component on the training set of anonymized images to generate the trained AI component;
train the AI component on the images of a plurality of persons to generate a reference trained AI component; and
validate the AI component by comparing performance of the trained AI component with performance of the reference trained AI component.

15. A non-transitory computer readable medium storing instructions executable by at least one electronic processor for performing a method of generating a training set of anonymized images for training an artificial intelligence (AI) component from images of a plurality of persons, the method comprising:

partitioning the images into P spatial regions to generate P sets of image patches corresponding to the P spatial regions;

assembling a set of training images in a common reference frame by, for each training image in the common reference frame, selecting an image patch from each of the P sets of image patches and assembling the selected image patches into the training image; and processing the training images in the common reference frame to generate the training set of anonymized images.

16. The non-transitory computer readable medium of claim 15, wherein the method further includes:

spatially mapping the images of the plurality of persons to a reference image to generate images in a common reference frame;

wherein the partitioning, assembling, and processing are performed in the common reference frame.

17. The non-transitory computer readable medium of claim 15, wherein the processing includes:

applying statistical inverse spatial mappings to the training images in the common reference frame, wherein the statistical inverse spatial mappings are derived from spatial mappings of the images of the plurality of persons to the reference image.

18. The non-transitory computer readable medium of claim 17, wherein the applying includes:

inverting the spatial mappings of the images of the plurality of persons to the reference image to form to a set of inverse spatial mappings, and randomly or pseudorandomly selecting the statistical inverse spatial mappings from the set of inverse spatial mappings.

19. The non-transitory computer readable medium of claim 17, wherein the applying includes:

computing statistical distributions of parameters of the spatial mappings of the images of the plurality of persons to the reference image to form to a set of inverse spatial mappings; and generating the statistical inverse spatial mappings based on the statistical distributions of parameters of the spatial mappings of the images of the plurality of persons to the reference image.

20. A method of generating a training set of anonymized images for training an artificial intelligence (AI) component from images of a plurality of persons, the method comprising:

partitioning the images into P spatial regions to generate P sets of image patches corresponding to the P spatial regions;

assembling a set of training images in a common reference frame by, for each training image in the common reference frame, selecting an image patch from each of the P sets of image patches and assembling the selected image patches into the training image;

processing the training images in the common reference frame to generate the training set of anonymized images; and training the AI component on the training set of anonymized images.

* * * * *